US009020600B2

(12) United States Patent
Lipson et al.

(10) Patent No.: US 9,020,600 B2
(45) Date of Patent: Apr. 28, 2015

(54) MAGNETIC CONTROL OF EYELID POSITION

(75) Inventors: David Lipson, Ithaca, NY (US); Gary J. Lelli, Jr., New York, NY (US); Mark Rosenblatt, New York, NY (US); Rohini Rao, Plainsboro, NJ (US); Nadee Nissanka, Osprey, FL (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/995,024

(22) PCT Filed: Dec. 16, 2011

(86) PCT No.: PCT/US2011/065544
§ 371 (c)(1),
(2), (4) Date: Jun. 17, 2013

(87) PCT Pub. No.: WO2012/083195
PCT Pub. Date: Jun. 21, 2012

(65) Prior Publication Data
US 2013/0274541 A1   Oct. 17, 2013

Related U.S. Application Data

(60) Provisional application No. 61/424,429, filed on Dec. 17, 2010.

(51) Int. Cl.
*A61N 1/00* (2006.01)
*A61F 9/007* (2006.01)
*G02C 11/00* (2006.01)
*A61N 2/00* (2006.01)
*A61N 2/02* (2006.01)
*A61N 2/06* (2006.01)

(52) U.S. Cl.
CPC ............ *A61F 9/00718* (2013.01); *G02C 11/00* (2013.01); *G02C 2200/02* (2013.01); *A61N 2/004* (2013.01); *A61N 2/02* (2013.01); *A61N 2/06* (2013.01)

(58) Field of Classification Search
USPC ................................ 607/48; 600/25; 128/419
See application file for complete search history.

(56) References Cited

U.S. PATENT DOCUMENTS

| 4,799,487 A * | 1/1989 | Bleicher ........................ 607/48 |
| 5,389,981 A * | 2/1995 | Riach, Jr. ...................... 351/158 |
| 5,542,437 A | 8/1996 | Blackmore et al. |
| 5,823,938 A | 10/1998 | Hernandez |
| 2002/0183587 A1 * | 12/2002 | Dormer ......................... 600/25 |
| 2006/0069420 A1 | 3/2006 | Rademacher et al. |
| 2007/0031761 A1 | 2/2007 | Kohl et al. |
| 2011/0031431 A1 | 2/2011 | Hull et al. |

OTHER PUBLICATIONS

De Maio, M., "Use of botulinum toxin in facial paralysis" Journal of Cosmetic & Laser Therapy (2003) pp. 216-217, vol. 5.

(Continued)

*Primary Examiner* — Robert N Wieland
(74) *Attorney, Agent, or Firm* — Scully, Scott, Murphy & Presser, P.C.

(57) ABSTRACT

Methods, devices, and kits comprising a magnetic system for automation of blinking, or to provide temporary or permanent assistance with opening or closure of the eyelids to treat disorders of the eyelids, including lagophthalmos and ptosis.

17 Claims, 7 Drawing Sheets

(56) References Cited

OTHER PUBLICATIONS

Demirci, H. et al., "Palpebral spring in the management of lagophthalmos and exposure keratopathy secondary to facial nerve palsy" Ophthal Plast Reconstr Surg (2009) pp. 270-275, vol. 25, No. 4.

Demirci, H. et al., "Graded full-thickness anterior blepharotomy for correction of upper eyelid retraction not associated with thyroid eye disease" Ophthalmic Plastic Reconstructive Surgery (2007) pp. 39-45, vol. 23, No. 1.

Frueh, B.R. et al., "Levator force generation in normal subjects" Trans Am Ophthalmol Soc (1990) pp. 109-119, vol. 88.

Hassan, A.S. et al., "Mallerectonny for upper eyelid retraction and lagophthalmos due to facial nerve palsy" Arch Ophthalmol (Sep. 2005) pp. 1221-1225, vol. 123.

Adams, W.M., "The use of masseter, temporalis and frontalis muscles in the correction of facial paralysis" Plastic & Reconstructive Surgery (1946) pp. 216-228, vol. 1.

Mancini, R. et al., "Use of hyaluronic acid gel in the management of paralytic lagophthalmos: the hyaluronic acid gel gold weight" Ophtha Plast Reconstr Surg (2009) pp. 23-26, vol. 25, No. 1.

Mansolf, F.A., "Techniques for the repair of orbicularis oculi palsy" Ophthalmic Surg (1978) pp. 67-70, vol. 19.

Lessa, S. et al., "Treatment of Paralytic Lagophthalmos with Gold Weight Implants Covered by Levator Aponeurosis" Ophthal Plast Reconstr Surg (2009) pp. 189-193, vol. 25, No. 3.

Moskowitz, L.R. "Permanent Magnet Design and Application Handbook" Krieger Publishing Company, Malabar, FL (1995) pp. 68-69.

Mühlbauer, W.D. et al., "Restoration of lid functon in facial palsy with permanent magnets" Chir plastic (Berlin) (1973) pp. 295-304, vol. 1.

Peitersen, E., "Bell's palsy: the spontaneous course of 2,500 peripheral facial nerve palsies of different etiologies" Acta Otolaryngol (2002) pp. 4-30, vol. Suppl 549.

Pirrello, R. et al., "Static treatment of paralytic lagophthalmos with autogenous tissues" Aesth Plast Surg. (2007) pp. 725-731, vol. 31.

Riehm, E. et al., "Experience with magnet implantation in lagophthalmos" Klin Mbl Augenheilk (1976) pp. 524-528, vol. 169, together with English language abstract.

Seiff, S.R. et al., "The staged management of ophthalmic complications of facial nerve palsy" Ophthal Plast Reconstr Surg (1993) pp. 241-249, vol. 9, No. 4.

Silver, A.L. et al., "Thin profile platinum eyelid weighting: a superior option in the paralyzed eye" Plastic and Reconstr Surg. (Jun. 2009) pp. 1697-1703, vol. 123, No. 6.

International Search Report dated Jul. 27, 2012 issued in International Application No. PCT/US2011/065544.

\* cited by examiner

A

B

MAGNETIC CONTROL OF EYELID POSITION

CROSS-REFERENCE TO RELATED APPLICATIONS

This application claims the benefit of and priority to U.S. Provisional Application Ser. No. 61/424,429 filed Dec. 17, 2010.

BACKGROUND

Lagophthalmos commonly results in exposure keratopathy and may lead to corneal ulceration, and globe perforation. While most often a result of de-innervation of the orbicularis oculi, the resulting exposure may be directly caused by upper eyelid retraction (unopposed protractors), decreased blink excursion or frequency and/or lower eyelid ectropion. Initial management is supportive consisting of the frequent use of ocular lubricants. Additional conservative options include eyelid taping, bandage contact lenses, moisture chambers, adhesive eyelid weights, botulinum toxin, and hyaluronic acid gel (De Maio M. Use of botulinum toxin in facial paralysis. *J Cosmet Laser Ther* 2003; 5:216-7; Mancini R, et al. Use of hyaluronic acid gel in the management of paralytic lagophthalmos: the hyaluronic acid gel "gold weight. *Ophtha Plast Reconstr Surg* 2009; 25(1):23-26.). Often, despite aggressive conservative therapy, the exposure keratopathy progresses and a temporary or permanent surgical alternative is sought.

Traditionally, surgical interventions for the short term include temporary medial and/or lateral tarsorrhaphies. However, this technique often requires repeated suturing secondary to eyelid inflammatory responses to the suture material. Additionally, it is not simple to temporarily reverse, thereby causing distorted eyelid anatomy in public settings and making ophthalmic examination more difficult (Mansolf F A. Techniques for the repair of orbicularis oculi palsy. *Ophthalmic Surg* 1978 19:67-70; Lessa S, et al *Ophthal Plast Reconstr Surg* 2009; 25 (3): 189-193.). Permanent lateral and medial tarsorrhaphies have similar limitations, and, in a more permanent fashion, decrease patient cosmesis.

Other surgical options reported include temporalis or masseter muscle flaps, fascia lata grafts, and direct facial or autogenous nerve grafts. Unfortunately, these techniques result in distortion of palpebral fissure anatomy, impair spontaneous blinking, require more than one surgical step, and are significantly more complex technically (Lessa et al 2009; Adams W M. The use of masseter, temporalis and frontalis muscles in the correction of facial paralysis. *Plast Reconstr Surg* 1946; 1:216-28. Pirello R, D'Arpa S, Moschella F. Static treatment of paralytic lagophthalmos with autogenous tissues. *Aesth Plast Surg.* 2007; 31:725-31; Seiff S R and Chang J S Jr. The staged management of ophthalmic complications of facial nerve palsy. *Ophthal Plast Reconstr Surg* 1993; 9:241-9).

There are many other techniques for upper eyelid lowering, which include müllerectomy, full-thickness blepharotomy, transcutaneous or transconjunctival levator recession and levator marginal myotomy. While these techniques can sufficiently treat patients with facial nerve palsy, they are static in nature and are limited in the amount of the corneal protection they can provide. (Seiff and Chang 1993; Hassan A S et al. Müllerectomy for upper eyelid retraction and lagophthalmos due to facial nerve palsy. *Arch Ophthalmol* 2005; 123:1221-5; Demirci H, et al. Graded full-thickness anterior blepharotomy for correction of upper eyelid retraction not associated with thyroid eye disease. *Ophthal Plast Reconstr Surg* 2007: 23:39-45; Demirci H and Frueh B. Palpebral spring in the management of lagophthalmos and exposure keratopathy secondary to facial nerve palsy. *Ophthal Plast Reconstr Surg* 2009: 25(4):270-5.)

Reconstruction techniques have can also involve implantation. Silicone encircling bands allow for dynamic lid closure, but have been abandoned due to difficulty in balancing band tension with levator palpebrae muscle force, along with a limited life span of about 6 months (Lessa et al 2009; Seiff and Chang 1993; Hassan et al 2005). Palpebral springs also allow for dynamic lid closure with the possibility for individualized height adjustment, but have the disadvantage of metal fatigue, dislocation, extrusion, and granuloma formation (Demirci et al 2007; Mansolf 1978).

The most frequently used technique, eyelid-loading with a metal weight, has its complications as well. Although gold is considered to be an unlikely allergen, there is still risk of allergy, in addition to extrusion, eyelid distortion, induced astigmatism, nocturnal lagophthalmos, undercorrection or overcorrection with resultant residual lagophthalmos or blepharoptosis, respectively. Furthermore, complete facial nerve recovery can occur in 21-83% patients, depending on the etiology, which can necessitate weight removal (Peitersen E. Bell's palsy: the spontaneous course of 2,500 peripheral facial nerve palsies of different etiologies. *Acta Otolaryngol Suppl* 2002:4-30). Platinum weights offer lower profiles and may be an option for patients with documented gold allergies (Silver A L, Lindsay R W et al. Thin profile platinum eyelid weighting: a superior option in the paralyzed eye. *Plastic and Reconstr Surg.* 2009; 123 (6): 1697-1703).

In 1973, Mühlbauer et al published a procedure that used magnetic implants into the upper and lower eyelid to afford closure (Mühlbauer W D, Segeth H, Viessmann A. Restoration of lid function in facial palsy with permanent magnets. *Chir plastic (Berlin)* 1973; 1:295.). Several years later, Riehm et al published promising data in 29 patients using this method (Riehm E, Hinzpeter E N. Experience with magnet implantation in lagophthalmos. *Klin Mbl Augenheilk.* 1976; 169: 524-8.).

Patients may also suffer conditions or diseases in which they cannot open their eyelids fully, a condition known as ptosis. Ptosis may be caused by damage/trauma to the muscle which raises the eyelid, damage to the superior cervical sympathetic ganglion or damage to the nerve (3rd cranial nerve (oculomotor nerve)) which controls this muscle. Such damage could be a sign or symptom of an underlying disease such as diabetes mellitus, a brain tumor, and diseases which may cause weakness in muscles or nerve damage, such as myasthenia gravis. Exposure to the toxins in some snake venoms, such as that of the black mamba, may also cause this effect. Ptosis may be due to a myogenic, neurogenic, aponeurotic, mechanical or traumatic cause and it usually occurs isolated, but may be associated with various other conditions, like immunological, degenerative, or hereditary disorders, tumors, or infections.

Ptosis may require surgical correction if severe enough to interfere with vision or if cosmesis is a concern. Treatment depends on the type of ptosis and is usually performed by an ophthalmic plastic and reconstructive surgeon, specializing in diseases and problems of the eyelid. Surgical procedures include Levator resection, Müller muscle resection, and Frontalis sling operation. Non-surgical modalities like the use of "crutch" glasses or special Scleral contact lenses to support the eyelid may also be used. Mühlbauer et al also tested their implanted double magnet systems in rabbit models of ptosis with promising results. They placed one magnet on the lower margin of the upper eyelid, and the other along the upper orbital rim firmly fixed to the periosteum. (Muehlbauer et al 1973).

SUMMARY

The management of lagophthalmos is complicated by its unpredictable course and accordingly, there is a demand for a solution that is effective, adjustable, and that may be deployed on a temporary or longer term basis.

Additionally, there is a demand for a solution for ptosis that is effective, adjustable, and that may be deployed on a temporary or long term basis.

Disclosed are methods and devices that involve utilization of a magnetic system for automation of blinking, or for temporary or permanent opening or closure of the eyelids.

Methods to treat an eyelid disorder are provided, comprising affixing magnetic material to lower rim of the upper eyelid; affixing magnetic material to the surface of the upper rim of the lower eyelid or to surface of the upper orbital rim; and allowing the force of the magnetic field to move the upper and lower eyelid or the upper eyelid. The magnetic material may be affixed to the surface of the lower rim of the upper eyelid. The magnetic material may be implanted within the lower rim of the upper eyelid. The disorder may be lagophthalmos and a magnet may be affixed to the lower rim of the upper eyelid and another magnet to the surface of the upper rim of the lower eyelid, and the magnets may pull the eyelid closed. The disorder may be ptosis and a magnet may be affixed to the lower rim of the upper eyelid and another magnet to the surface of the upper orbital rim and the magnets may pull the eyelid open.

Methods to treat an eyelid disorder are provided, comprising: affixing magnetic material to the lower rim of the upper eyelid; providing an eye covering device into which magnetic material has been incorporated or onto which magnetic material is affixed; and allowing the force of the magnetic field to move the upper eyelid. The eye covering device may be selected from the group comprising an electromagnetic eye covering device, eyeglass frames, goggles, a mask, or a patch. The magnetic material including, but not limited to, magnetic cosmetic type powder may be affixed to the surface of the lower rim of the upper eyelid. The magnetic material may be implanted within the lower rim of the upper eyelid. The disorder may be lagophthalmos and the magnetic material may be affixed to the lower rim of the upper eyelid and another magnet may be incorporated into or affixed to a lower region of an eye covering device and the magnets may pull the eyelid closed. The disorder may be ptosis and a magnet may be affixed to the lower rim of the upper eyelid and another magnet may be incorporated into or affixed to an upper region of an eye covering device and the magnets may pull the eyelid open.

Also disclosed is a device comprising:
an eye covering device;
an electromagnet incorporated into or affixed to the eye covering device;
a control circuit in communication with the electromagnet and configured to tune the electromagnet to generate a field to open or close an eyelid which is associated with a magnet;
a power supply coupled to the control circuit configured to supply power to the electromagnet under control of the control circuit; and
a user interface associated with the control circuit configured to receive a user generated control command.

A kit is provided, comprising: a set of pieces of magnetic material of appropriate size for affixation to an eyelid or orbital rim, and adhesive appropriate for atraumatic temporary affixation of the magnetic material to skin. The kit further comprises instructions for using the magnetic material and adhesive for treating an eyelid disorder.

A kit is provided, comprising: a set of r pieces of magnetic material of appropriate size for affixation to an eyelid or orbital rim, an eye covering device, and adhesive appropriate for atraumatic temporary affixation of the magnetic material to skin. The kit further comprises instructions for using the magnetic material, eye covering device, and adhesive for treating an eyelid disorder. Magnetic material may be incorporated into or affixed to the eye covering device.

Also disclosed is a kit comprising: magnetic powder configured for application to an eyelid or orbital rim and an eye covering device.

DETAILED DESCRIPTION

Figure 1:
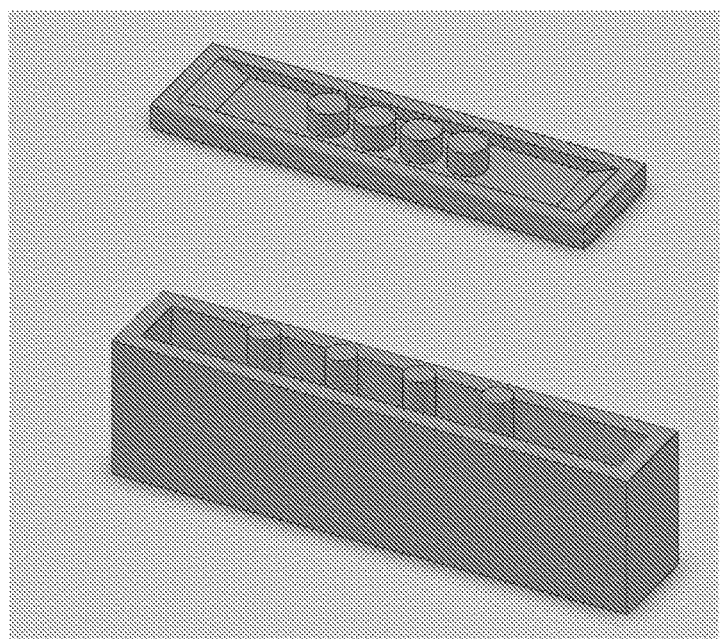
FIG. 1. Disk magnet mold and Cylinder magnet mold.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The new methods and devices utilize a magnetic system for automation of blinking, or to provide temporary or permanent assistance with opening or closure of the eyelids to treat disorders of the eyelids, including lagophthalmos and ptosis.

Methods To Treat Lagophthalmos

In one embodiment, a method to treat lagophthalmos is described. At least one magnet is affixed to the surface of the lower rim of the upper eyelid. At least one magnet is affixed to the surface of upper rim of the lower eyelid. Any permanent magnet known in the art may be used; in some embodiments, the magnet may be comprised of Alnico5 or neodymium. Combinations of magnets may be used. The magnets may be placed so that the pole of the at least one magnet on one eyelid faces the opposing pole of the at least one magnet on the opposing lid, and the magnets thereby attract one another. Magnetic material may also be affixed to either or both of the lower rim of the upper eyelid and upper rim of the lower eyelid. Magnetic material is material that is susceptible to magnetism but may or may not be permanently magnetized. Any magnetic material known in the art, such as ferrite, may be used. The magnet and magnetic material may be solid, or may be in the form of particles or larger pieces embedded in another substance. For example, the magnet and magnetic material may be in the form of particles embedded in a fiber as is known in the art (for example, U.S. Patent Application 20110031431—Magnetic Composite Structures with High Mechanical Strength; see also U.S. Application Patent Application 200700031761—Fibers excellent in magnetic field responsiveness and conductivity and product consisting of it). For example, the fibers can be applied in the form of a tape. The fibers can be nanofibers manufactured using directed assembly techniques and external field to create the fibers having catalytic, magnetic and electrical properties. The magnet and/or magnetic material, in solid or particle form, may be embedded in or coated with a bicompatible substance, such as for example silicone.

Additionally, a polymer prosthesis using urethane can be used. Ferrite resistors are candidates because of their size and magnetic properties. Additionally, the ferrite resistors can be magnetized after the prosthesis is completed. Additionally, magnetic powder can be used either separately or together with the above polymers. The magnetic powers, such as samarium cobalt, can be formed into a very small size and embedded in the polymers, and magnetized after. Further, a magnetic eyeshadow or makeup powder can be used. A magnetic material is infused, added or embedded into the eye shadow or makeup powder. The magnetic powder can be applied by painting the powder on the upper or lower eyelids.

The magnet and magnetic material may be affixed to the skin with adhesive. Said adhesive may be in the form of tape that is placed over the magnet or double stick tape that is placed between the magnet and/or magnetic material and the skin. The adhesive may be in the form or a paste, gel, or liquid and may be provided upon one a surface of the magnet or maybe in a separate container. The adhesive is appropriate for atraumatic temporary affixation of said magnets to skin, as is known in the art.

In another embodiment, a method to treat lagophthalmos is described. At least one magnet is affixed to the surface of the lower rim of the upper eyelid or to the surface of upper rim of the lower eyelid. Magnetic material is affixed to the surface to which the magnet is not placed; magnetic material is affixed to the surface of the lower rim of the upper eyelid if the magnet is placed on the upper rim of the lower eyelid; alternatively magnetic material is affixed to the surface of the upper rim of the lower eyelid if the magnet is placed on the surface of the lower rim of the upper eyelid. The magnet, magnetic material, and adhesive may be in the forms already described herein.

In another embodiment, a method to treat lagophthalmos is described. At least one magnet is affixed to the surface of the lower rim of the upper eyelid. At least one magnet is affixed to the surface of the upper orbital rim. The magnets may be placed so that the pole of the at least one magnet on one eyelid faces the same pole of the at least one magnet on the opposing lid, and the magnets thereby repel one another. Magnetic material may also be affixed to either or both of the lower rim of the upper eyelid and the upper orbital rim. The magnet, magnetic material, and adhesive may be in the forms already described herein.

In another embodiment, a method to treat lagophthalmos is described. At least one magnet is affixed to the surface of the lower rim of the upper eyelid. At least one magnet is affixed to the surface of the upper orbital rim. The magnets may be placed so that the pole of the at least one magnet on one eyelid faces the same pole of the at least one magnet on the opposing lid, and the magnets thereby repel one another. Magnetic material may also be affixed to either or both of the lower rim of the upper eyelid and/or the upper orbital rim. The magnet, magnetic material, and adhesive may be in the forms already described herein.

In another embodiment, a method to treat lagophthalmos is described. At least one magnet is affixed to the surface of the lower rim of the upper eyelid. An eye covering device, which may be any eye covering device known in the art, including eyeglasses (including electromagnetic eye covering device as described herein), a mask, goggles, an eyepatch, or the like) are provided which have at least one magnet incorporated into or affixed at or near a lower region, which may include a lower edge. The lens of the eye covering device, if any are present, may be any lens, including prescription lenses, or reading lenses of any power, no correction, shaded lenses, or polarized lenses, or any combination thereof. The magnets may be placed so that the pole of the at least one magnet on lower rim of the upper eyelid faces the opposing pole of the at least one magnet on the eye covering device, and the magnets thereby attract one another. Magnetic material may also be affixed to either or both of the lower rim of the upper eyelid or lower region of the eye covering device. Alternatively, either the magnet on the lower rim of the upper eyelid or the magnet incorporated into or affixed to the eye covering device may be replaced with magnetic material. The magnet, magnetic material, and adhesive may be in the forms already described herein. Alternatively, either the magnet on the lower rim of the upper eyelid or the magnet incorporated into or affixed to the eye covering device may be replaced with magnetic material.

In another embodiment, a method to treat lagophthalmos is described. At least one magnet is affixed to the surface of the lower rim of the upper eyelid. An eye covering device is provided, which has at least one magnet incorporated into or affixed at or near an upper region, which may include an upper edge. The magnets may be placed so that the pole of the at least one magnet on lower rim of the upper eyelid faces the same pole of the at least one magnet on the eye covering device, and the magnets thereby repel one another. Magnetic material may also be affixed to either or both of the lower rim of the upper eyelid and/or the eye covering device. The eye covering device, magnet, magnetic material, and adhesive may be in the forms already described herein.

In another embodiment, a method to treat lagophthalmos is described. At least one magnet is surgically implanted within the upper eyelid. At least one magnet may be affixed to the surface of upper rim of the lower eyelid, or an eye covering device may be provided, which has magnets incorporated into or affixed at or near a lower region, which may include a lower edge. The magnets may be placed so that the pole of the at least one magnet in the upper eyelid faces the opposite pole of the at least one magnet on the lower eyelid or on the lower region of the eye covering device, and the magnets thereby attract one another. Magnetic material may also be affixed to the upper rim of the lower eyelid or included with the magnet implanted in the upper eyelid or eye covering device. The eye covering device, magnet, magnetic material, and adhesive may be in the forms already described herein.

In another embodiment, a method to treat lagophthalmos is described. At least one magnet is surgically implanted within the upper eyelid. At least one magnet may be affixed to the surface of the upper orbital rim, or an eye covering device may be provided, which has at least one magnet incorporated into or affixed at or near an upper region, which region may include an upper edge. The magnets may be placed so that the pole of the at least one magnet in the upper eyelid faces the same pole of the at least one magnet on the upper orbital rim or on the upper region of the eye covering device, and the magnets thereby repel one another. Magnetic material may also be affixed to the upper orbital rim or eye covering device, or included with the magnet implanted in the upper eyelid. The eye covering device, magnet, magnetic material, and adhesive may be in the forms already described herein.

Methods to Treat Ptosis

In another embodiment, a method to treat ptosis is described. At least one magnet is affixed to the surface of the upper orbital rim. At least one magnet is affixed to the surface of upper rim of the lower eyelid. The magnets may be placed so that the pole of the at least one magnet on one eyelid faces the opposite pole of the at least one magnet on the upper orbital rim, and the magnets thereby attract one another. Magnetic material may also be affixed to either or both of the lower rim of the upper eyelid and the upper orbital rim. The magnet, magnetic material, and adhesive may be in the forms already described herein.

In another embodiment, a method to treat ptosis is described. At least one magnet is affixed to the surface of the lower rim of the upper eyelid. At least one magnet is affixed to the surface of upper rim of the lower eyelid. The magnets may be placed so that the pole of the at least one magnet on one eyelid faces the same pole of the at least one magnet on the opposing lid, and the magnets thereby repel one another. Magnetic material may also be affixed to either or both of the lower rim of the upper eyelid and the upper rim of the lower eyelid. The magnet, magnetic material, and adhesive may be in the forms already described herein.

In another embodiment, a method to treat ptosis is described. At least one magnet is affixed to the surface of the lower rim of the upper eyelid. An eye covering device is provided, which has at least one magnet incorporated into or affixed at or near a lower region, which may include a lower edge. The magnets may be placed so that the pole of the at least one magnet on lower rim of the upper eyelid faces the same pole of the at least one magnet on the eye covering device and the magnets thereby repel one another. Magnetic material may also be affixed to either or both of the lower rim of the upper eyelid or lower region of the eye covering device. The eye covering device, magnet, magnetic material, and adhesive may be in the forms already described herein.

In another embodiment, a method to treat ptosis is described. At least one magnet is affixed to the surface of the lower rim of the upper eyelid. An eye covering device is provided, which has at least one magnet incorporated into or affixed to an upper region, which may include an upper edge. The magnets are placed so that the pole of the at least one magnet on lower rim of the upper eyelid faces the opposite pole of the at least one magnet on the eye covering device, and the magnets thereby attract one another. Magnetic material may also be affixed to either or both of the lower rim of the upper eyelid and an upper region eye covering device. Alternatively, either the magnet on the lower rim of the upper eyelid or the magnet incorporated into or affixed to the eye covering device may be replaced with magnetic material. The eye covering device, magnet, magnetic material, and adhesive may be in the forms already described herein.

In another embodiment, a method to treat ptosis is described. At least one magnet is surgically implanted within the upper eyelid. At least one magnet may be affixed to the surface of upper rim of the lower eyelid, or an eye covering device may be worn, which has at least one magnet incorporated into or affixed at or near a lower region, which may include a lower edge. The magnets may be placed so that the pole of the at least one magnet in the upper eyelid faces the same pole of the at least one magnet on the lower eyelid or on the lower edge of the eye covering device, and the magnets thereby repel one another. Magnetic material may also be affixed to the lower edge of the eye covering device, or included with the magnet implanted in the upper eyelid. The eye covering device, magnet, magnetic material, and adhesive may be in the forms already described herein.

In another embodiment, a method to treat ptosis is described. At least one magnet is surgically implanted within the upper eyelid. At least one magnet may be affixed to the surface of the upper orbital rim, or an eye covering device may be worn, which has at least one magnet incorporated into or affixed at or near an upper region, which may include an upper edge. The magnets may be placed so that the pole of the at least one magnet in the upper eyelid faces the opposite pole of the at least one magnet on the surface of the upper orbital rim or on the upper region of the eye covering device, and the magnets thereby attract one another. Magnetic material may also be affixed to the upper orbital rim or eye covering device, or included with the magnet implanted in the upper eyelid. The eye covering device, magnet, magnetic material, and adhesive may be in the forms already described herein.

In another embodiment, a method to treat a disorder involving an inability to close or open an eyelid, where the eyelid is capable of being manually opened or closed, is described. At least one magnet is surgically implanted within the upper eyelid, or is affixed to the surface of the upper eyelid. An electromagnetic eye covering device as described below are provided. The electromagnetic eye covering device is powered, and the control circuit of the electromagnetic eye covering device is tuned via the interface such that there is sufficient and appropriately oriented magnetic field to open and close the eyelid, and so that the natural, average rhythm of blinking is approximated.

Electromagnetic Eye Covering Device

Figure 7:
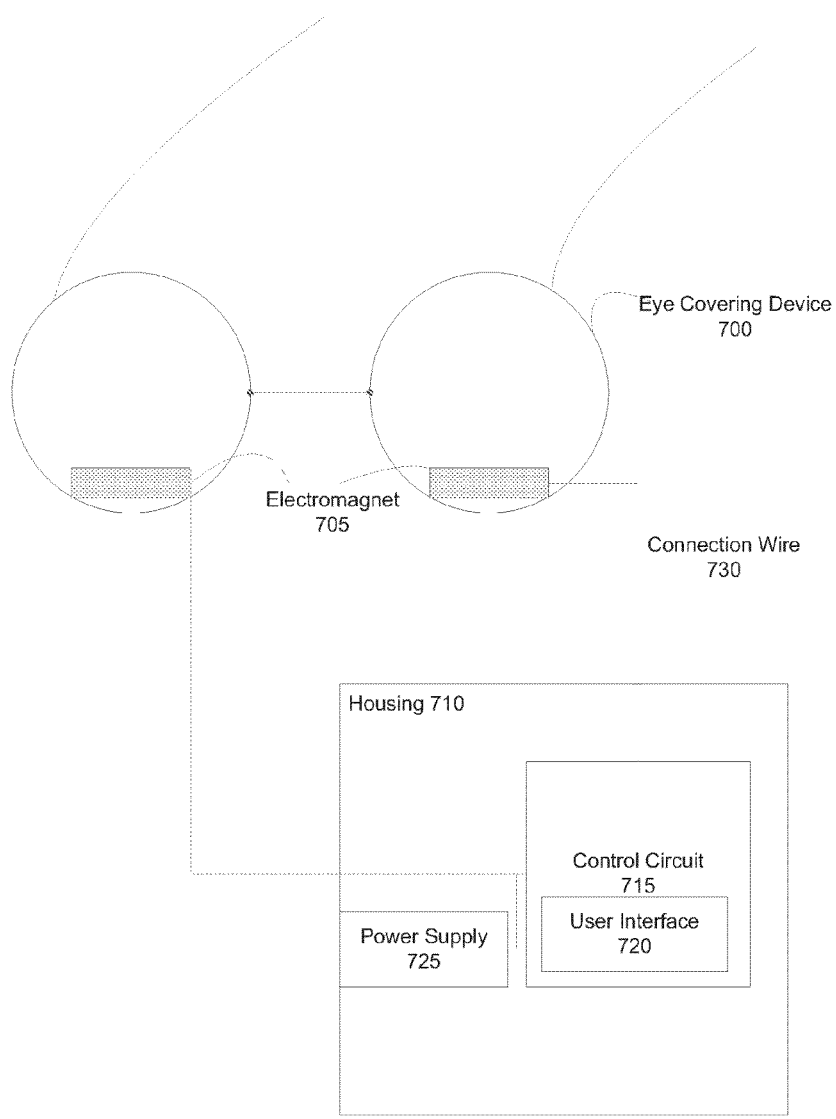
FIG. 7 illustrates an example of an electromagnetic eye covering device in accordance with the invention.

In another embodiment, an electromagnetic eye covering device is provided. FIG. 7 illustrates an example of the electromagnetic eye covering device. However, an electromagnetic eye covering device is not limited to the configuration depicted in FIG. 7 The electromagnetic eye covering device may comprise an eye covering device 700, such as an eyeglass frame, goggles, a patch or a mask, an electromagnet 705, a control circuit 715, and a power supply 725. The electromagnet 705, of any sort known in the art, may be affixed to, or incorporated into, the eye covering device. While electromagnets or solenoids are typically optimized for uniform fields, one of ordinary skill would realize that asymmetric fields would allow for focusing or concentrating the magnetic fields. A series of coils and ferrite cores can cause concentration of the magnetic fields. Alternatively, an internal linkage, rope, or rail mechanism could move magnets within the eye covering device 700, for example, around or along an eyeglass frame. The control circuitry, e.g., control circuit 715 may be affixed to, or incorporated into, the eye covering device, or may be connected to the eye covering device by wires or other means to carry current, as is known in the art. FIG. 7 depicts the control circuit 715 in a separate housing 710 from the eye covering device 700. The control circuit 715 being connected to the electromagnet 705 via a connection wire 730 or cable. The power supply 725 may be affixed to, or incorporated into, the eye covering device 700, or may be connected to the eye covering device 700 by wires or other means to carry current, known in the art. FIG. 7 depicts the power supply 725 in the same housing 710 as the control circuit 715. However, the power supply 725 can be in a different housing and coupled to the control circuit 715 using any known connection cable. The control circuit 715 may be similar to a capacitive discharge circuits used for electronic flash lamp, variations of which are well known in the art, with an added timer element. The control circuit 715 has an user interface 720 to allow a user to modulate the amplitude current and voltage produced by the control circuit 715, as well as the length of time said current and voltage are produced, as well as the direction of the current, as well as the length of time between current and voltage pulses. The user interface 720 may be analog, in the form of knobs or sliders or other means known in the art, or may be digital, and modulated through a software interface, which may in turn be controlled via a touchscreen. As depicted in FIG. 7, the user interface 720 is incorporated in the control circuit 715; however, the user interface 720 can be external to the control circuit 715 and coupled thereto. Furthermore, the control circuit 715 can include a receiver and the user interface 720 can communicate with the control circuit 715 via the receiver. The receiver can be a wired or wireless device. The control circuit 715 may be tuned via the user interface 720 such that there is sufficient magnetic field to open and close an upper eyelid into which a magnet or magnetic material has been implanted, or onto which a magnet or magnetic material has been affixed, and so that the natural, average rhythm of blinking is approximated. An average blink lasts approximately one tenth of a second, and people blink on average once every four seconds.

Kits

In another embodiment, a kit is provided, comprising a set of magnets and instructions. Markings may be on the surface of the magnets, indicating positive and negative poles. The magnets may be curvilinearly configured to align to the curvature of the upper eyelid and/or lower eyelid and/or upper orbital rim and/or an eye covering device. Different sizes of magnets may be provided so that the user of the kit may select a best fit. The magnets may be made of a flexible material or may be rigid. The magnets may have an adhesive coating on one side or may be embedded in or adhered to tape; alternatively adhesive may be provided as another element of the kit in the form of tape or in a container such as a tube. The adhesive is appropriate for atraumatic temporary affixation of said magnets to skin, as is known in the art. The magnets may be comprised of a solid block of magnet, or pieces of particles of magnets embedded in another substance. The magnets may comprise magnetic material. The eye covering device, magnet, magnetic material, and adhesive may be in the forms already described herein.

In another embodiment, a kit is provided, comprising a set of magnets, a set of parts comprised of magnetic material, and instructions. Markings may be on the surface of the magnets, indicating positive and negative poles. The magnets and magnetic material parts may be curvilinearly configured to align to the curvature of the upper eyelid and/or lower eyelid and/or upper orbital rim and/or eye covering device. Different sizes of magnets and magnetic material parts may be provided so that the user of the kit may select a best fit. The magnets and magnetic material parts may be made of a flexible material or may be rigid. The magnets and magnetic material parts may have an adhesive coating on one side or may be embedded in or adhered to tape; alternatively adhesive may be provided as another element of the kit in the form of tape or in a container such as a tube. The magnets may be comprised of a solid block of magnet, or pieces of particles of magnets embedded in another substance. The magnets may comprise magnetic material. The eye covering device, magnet, magnetic material, and adhesive may be in the forms already described herein.

In another embodiment, a kit is provided, comprising an eye covering device, a set of magnets, and instructions. The eye covering device may have at least one magnet incorporated into or affixed to a lower region, which may include a lower edge, or incorporated into or affixed to the upper region, including an upper edge. Markings may be on the surface of the magnets, indicating positive and negative poles. The magnets may be curvilinearly configured to align to the curvature of the upper eyelid and/or lower eyelid and/or upper orbital rim and/or eyeglass frame. Different sizes of magnets may be provided so that the user of the kit may select a best fit. The magnets may be made of a flexible material or may be rigid. The magnets may have an adhesive coating on one side or may be embedded in or adhered to tape; alternatively adhesive may be provided as another element of the kit in the form of tape or in a container such as a tube. The magnets may be comprised of a solid block of magnet, or pieces or particles of magnets embedded in another substance. The magnets may comprise magnetic material. The eye covering device, magnet, magnetic material, and adhesive may be in the forms already described herein.

In another embodiment, a kit is provided, comprising an eye covering device, a set of magnets or magnetic material, and instructions. The eye covering device may have at least one magnet, or magnetic material, incorporated into or affixed to a lower region, which may include a lower edge, or at least one magnet, or magnetic material, affixed to an upper region, which may include an upper edge. If magnets are incorporated or affixed to the eye covering device or if the eye covering device is an electromagnetic eye covering device as described herein, then magnetic material may be provided. If magnetic material is incorporated into or affixed to the eye covering device, magnets may be provided. The eye covering device, magnet, magnetic material, and adhesive may be in the forms already described herein.

In another embodiment, a kit is provided with magnetic powder such as eyeshadow or makeup and an eye covering device. The kit can also include instructions. The eye covering device may have at least one magnet, or magnetic material, incorporated into or affixed to a lower region, which may include a lower edge, or at least one magnet, or magnetic material, affixed to an upper region, which may include an upper edge. If magnets are incorporated or affixed to the eye covering device or if the eye covering device is an electromagnetic eye covering device as described herein, then magnetic material may be provided. If magnetic material is incorporated into or affixed to the eye covering device, magnets may be provided. The magnetic powder is applied to the eyelid. The application location will depend on the eyelid disorder and the corresponding location of the magnetic material or magnet on the eye covering device.

EXAMPLES

The present description is further illustrated by the following examples, which should not be construed as limiting in any way. The contents of all cited references (including literature references, issued patents, and published patent applications as cited throughout this application) are hereby expressly incorporated by reference.

Example 1

Making and Testing Embedded Magnets

The magnets were designed for three possible uses: external affixation to the upper and lower eyelids, implantation into the upper eyelid, and affixation to the lower rim of a pair of eyeglasses. The externally affixed upper and lower eyelid magnets allowed for testing in healthy volunteers and could also be a temporary solution for patients with paralytic lagophthalmos. A magnet on the upper eyelid, whether externally affixed or imbedded, with a magnet on the lower rim of a pair of glasses would be another possible configuration for patients. This design would give the patient the freedom to control the extent of eyelid closure by removal of the glasses. At night time, the patient could externally affix a magnet to the lower eyelid.

To avoid some of the difficulties with prior implantation methods, such as allergic reaction, migration, and extrusion, the magnets were imbedded in a biocompatible material, silicone. This material, also known as polydimethylsiloxane (PDMS), is made of 9 parts polydimethylsiloxane (PDMS) potting solution and one part PDMS catalyst. This material also allows the final product to be firmly implanted into an eyelid and flexible enough to fit to the customized curvature of individual lids. The molds to make the silicone encased magnets were designed through SolidWorks (http://www.solidworks.com), and created via Rapid Prototyping. Two different sizes were made for the two magnet shapes, disk and cylinder (Disk Magnet ⅛ inch by ¹⁄₃₂ inch, K&J Magnetics). (see FIG. 1).

In order to create the highest magnetic field possible with the smallest magnets, one of the strongest magnets commercially available (Neodymium) was used. Neodymium, which has a magnetic field of up to 16000 Gauss at the poles, was employed in conjunction with a wire brad made of soft steel. These two metals created a replica of the strongest magnetic configuration, the horseshoe shape magnet with a piece of steel (Moskowitz L R. Permanent Magnet Design and Application Handbook. Krieger Publishing Company, Malabar, Fla. 1995. Page 69.). While both the magnet or the steel wire brad could be placed on the upper lid, if these devices were implanted within the lid, it would be more convenient and safer for the steel wire brad to be implanted into the lid, as it would not interfere with subsequent magnetic resonance imaging.

Figure 2:
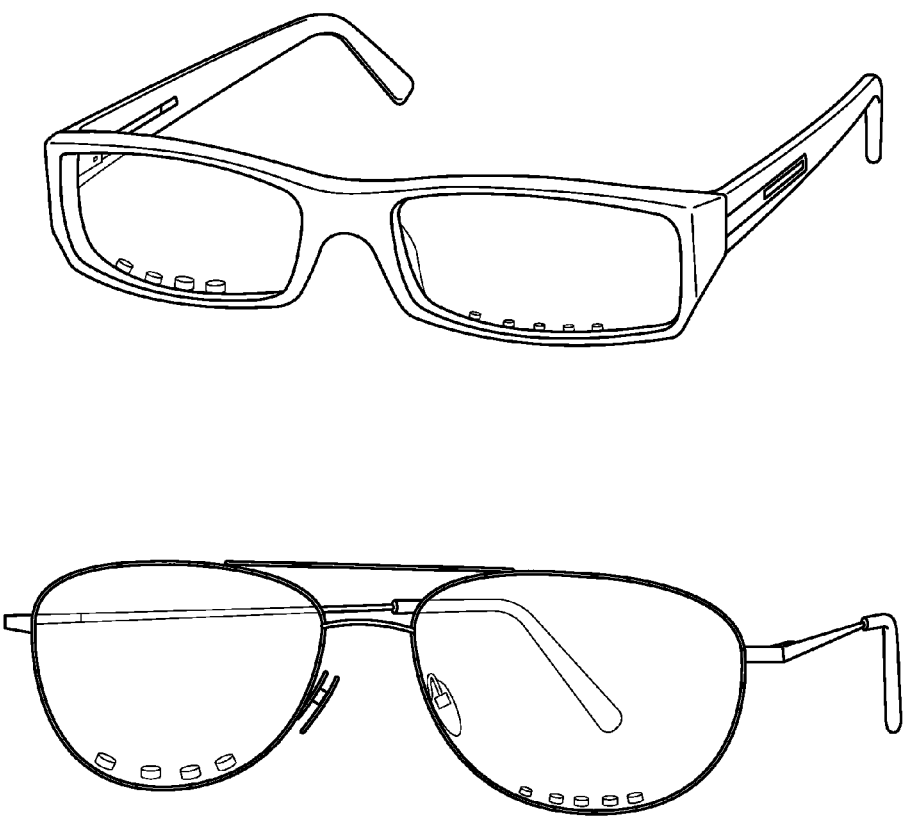
FIG. 2. Disk magnets on different spectacle frames. Squares indicate disk magnets with diameter of ⅛ inches and height of 1/32 inches. Circles indicate disk magnets with diameter of 1/16 inches and height of 1/32 inches.
Figure 3:
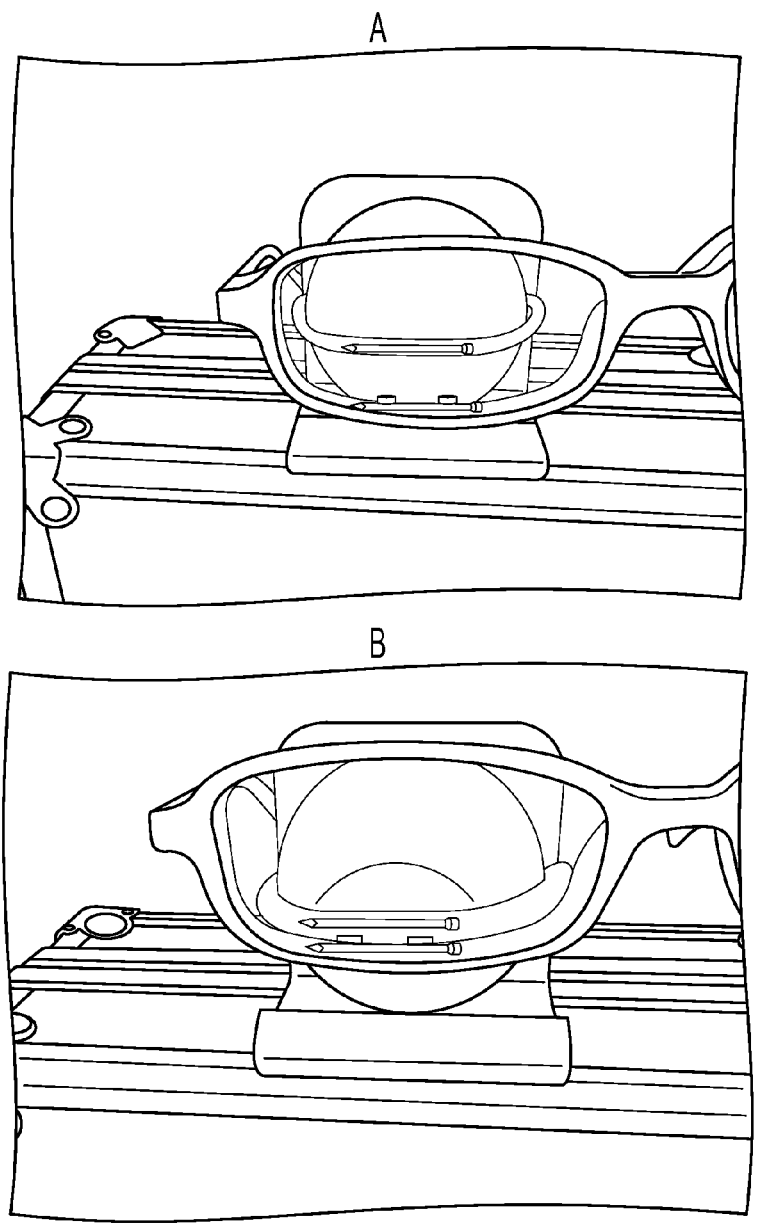
FIG. 3. Eyelid and eyeball model. A) eyelids in open position B) eyelids in closed position.

The lenses were removed from the two differently sized spectacle frames (Surplus Glasses) and magnets of two different sizes were used in each frame (see FIG. 2). Two large disk magnets (diameter ⅛ inch, height ¹⁄₃₂ inch) were placed on a wire brad (18 gauge by ¾ inch, 2 g, Lowes) to create a horseshoe magnet configuration. This, in turn was scored with sandpaper and secured to the spectacle rim with a multipurpose polyurethane adhesive (Gorilla Glue). A model of the eyelid was fashioned to allow for testing of the horseshoe magnet and steel piece. (FIG. 3).

Figure 4:
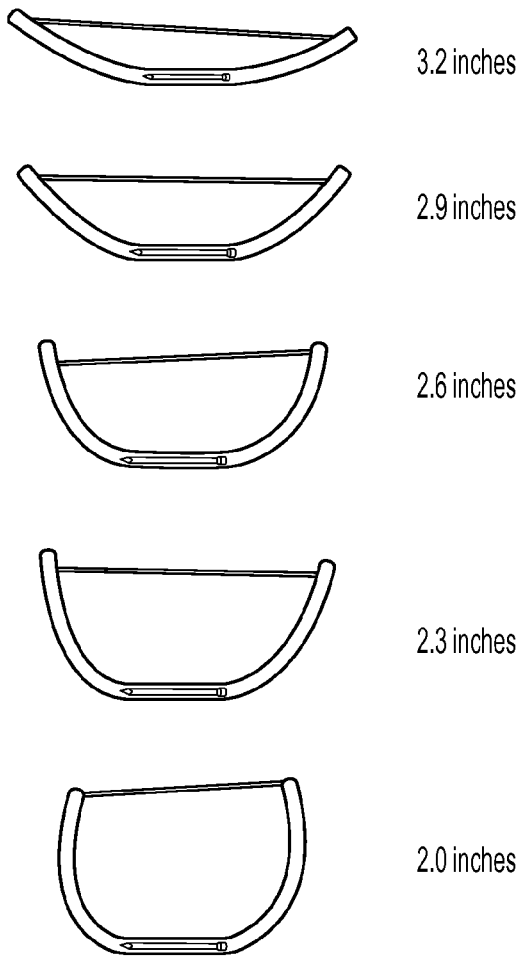
FIG. 4. Model eyelids of five different resting sizes, measured by the length of cord at rest.

Five different upper eyelid sizes were modeled using clear vinyl tubing and the steel wire brad in the center of the tubing (Vinyl Tubing EW-96480-00, Cole Parmer). The eyeball was modeled using a ping pong ball. Thus, the length of the vinyl tubing was measured to be half of the circumference of a ping pong ball. Each eyelid was made with different resting length of bead cord (Stretch Magic Clear Bead Cord™, 0.5 mm diameter, product #42326): 2.0 inches, 2.3 inches, 2.6 inches, 2.9 inches, 3.2 inches (see FIGS. 3 and 4).

In order to affix the magnet to the eyelid temporarily, double sided adhesive strip (EyeClose™ double sided adhesive strips, FCI Ophthalmics, Marshfield Hills, Mass., product #LL0505) was hand-fashioned to the appropriate shape.

Using magnetic formulas, the magnetic force between a horseshoe magnet (a steel backed disk magnet) and a wire brad (steel) was calculated using the specifications of diameter 3.175 mm, thickness 0.79375 mm, and distance 10 mm.

Results

Figure 5:
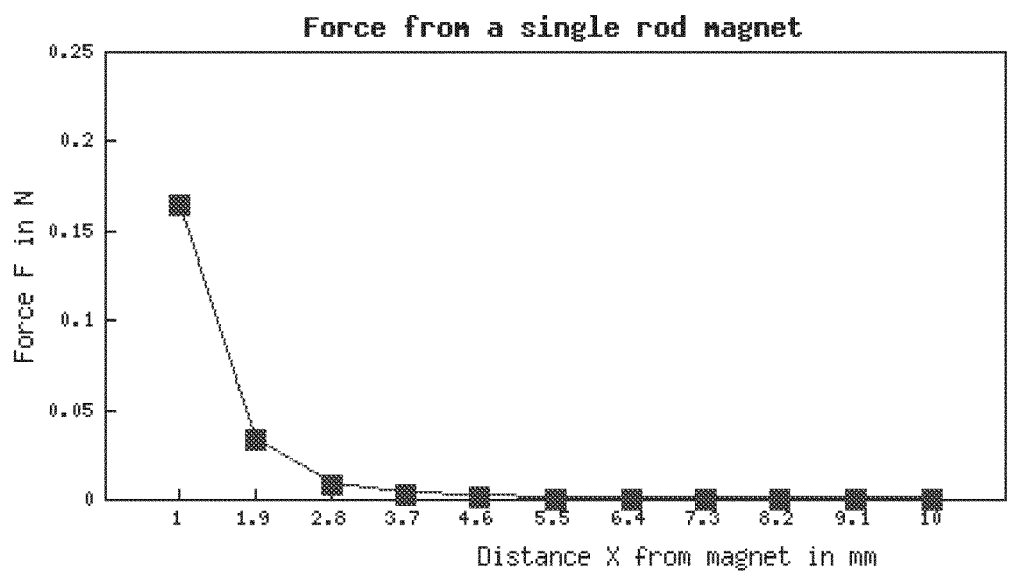
FIG. 5 A) Force created by a single rod magnet in relation to distance from piece of steel. B) Force created with steel wire diameter of 3.175 mm, thickness of 0.79375 mm with distance from magnet of 10 mm.
Figure 5:
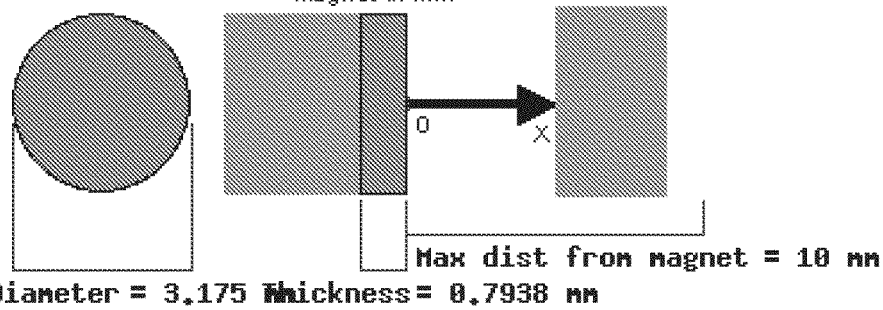

As the average levator muscle opening force of 75 grams, a magnetic formula was used to determine the number of magnets to close an eyelid (Frueh B R, Mush D C. Levator force generation in normal subjects. *Trans Am Ophthalmol Soc* 1990; 88:109-19.). With the horseshoe magnet and wire brad configuration, the maximum force at 1 mm is 17 grams, meaning at least four magnets would be required (FIG. 5).

Figure 6:
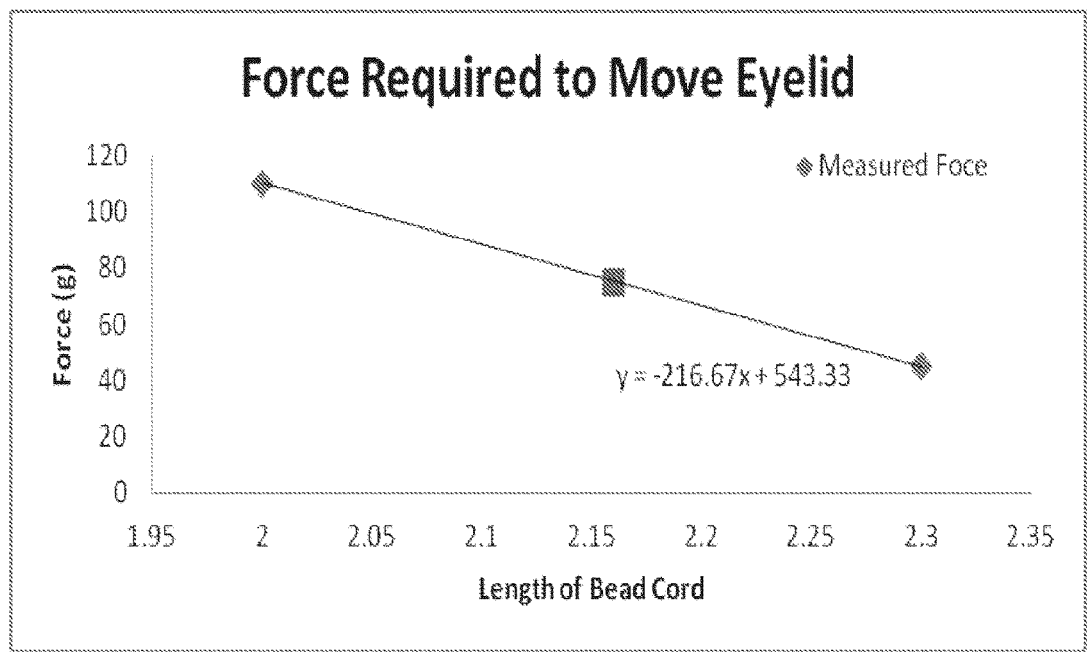
FIG. 6. Force required to move eyelid in relation to length of bead cord. Ideal Length to produce 75 grams of force is 2.16 inches.

In order to determine the optimal length of bead cord to model an eyelid, a spring force gauge with a maximum of 200 grams (McMaster-Carr) was used. For a 2.0 inch eyelid, 110 grams of force were required to move the eyelid. For the 2.3 inch eyelid, 45 grams of force were required. Extrapolating from this data, in order to produce the 75 grams of force to move the average eyelid, 2.16 inches of bead cord would be required (FIG. 6).

Prototypes for the molds were created using a three dimensional modeling program, called SolidWorks. An engineering design analysis software products and service, ANSYS, was used to demonstrate that four disk magnets or four cylindrical magnets on a spectacle rim (simulated as a bar magnet) would generate the 200 grams of force needed to far overcome the necessary 75 grams required. The first mold used ⅛ inch by ¹⁄₃₂ inch disk magnets and the second mold 1.5 mm by 5 mm cylindrical magnets Example 2

Human Testing of Surface Magnets

Purpose: To present a novel technique for the treatment of paralytic lagophthalmos and exposure keratopathy with an externally affixed magnetic system for tarsorrhaphy (MST). Methods: In conjunction with Cornell Bioengineering, magnets were set in silicone molds made of polydimethylsiloxane (PDMS) potting solution. The molds were created to be as thin as possible, curvilinear to approximate the normal eyelid architecture, and utilized 3M Medipore tape for applying the MST to the eyelid. In vivo testing of the MST was performed with 5 normal human volunteers. The following eyelid measurements were taken bilaterally in the subjects prior to any intervention: palpebral fissure (PF) and margin reflex distance to the upper (MRD1) and lower (MRD2) eyelids. Subsequently, the MST was affixed at the eyelid margin along the central eyelid and the eyelid measurements repeated at 5 minutes after placement.

Results: Prior to MST placement, palpebral fissure height (average+SD) was 9.8 mm+0.75. The margin reflex distance to the upper lid was 3.3 mm+0.6 and the margin reflex to the lower lid was 6.5 mm+0.32. After placement of the MST, palpebral fissure height was 2.4 mm+1.02. The margin reflex distance to the upper lid was 0.6 mm+1.04 and the margin reflex distance to the lower lid was 1.8 mm+0.4.

Conclusions: Surface magnets can generate sufficient force to effectively close eyelids.

What is claimed is:

1. A method to treat an eyelid disorder comprising:
   temporarily affixing non-particulate magnetic material to the surface of the lower rim of the upper eyelid;
   temporarily affixing non-particulate magnetic material to the surface of the upper rim of the lower eyelid or to surface of the upper orbital rim; and
   allowing the force of a magnetic field to move the upper and lower eyelids or the upper eyelid.

2. The method of claim 1 wherein the disorder is lagophthalmos and non-particulate magnetic material temporarily affixed to the lower rim of the upper eyelid and non-particulate magnetic material is temporarily affixed to the surface of the upper rim of the lower eyelid and the magnets pull the eyelid closed.

3. The method of claim 1 wherein the disorder is ptosis and a magnet is temporarily affixed to the lower rim of the upper eyelid and another magnet is affixed to the surface of the upper orbital rim and the magnets pull the eyelid open.

4. A method to treat an eyelid disorder comprising
   affixing magnetic material to the lower rim of the upper eyelid;
   providing an eye covering device into which electromagnetic material has been incorporated or onto which electromagnetic material is affixed, wherein the electromagnetic material can generate a magnetic field; and
   allowing the generated magnetic field to move the upper eyelid.

5. The method of claim 4 wherein the eye covering device is selected from the group consisting of an electromagnetic eye covering device, eyeglass frames, goggles, a mask, or a patch.

6. The method of claim 4, wherein the magnetic material is affixed to the surface of the lower rim of the upper eyelid.

7. The method of claim 4, wherein the magnetic material is implanted within the lower rim of the upper eyelid.

8. The method of claim 4 wherein the disorder is lagophthalmos and magnetic material is affixed to the lower rim of the upper eyelid and another magnet is incorporated into or affixed to a lower region of the eye covering device and the magnets pull the eyelid closed.

9. The method of claim 4 wherein the disorder is ptosis and a magnet is affixed to the lower rim of the upper eyelid and another magnet is incorporated into or affixed to an upper region of the eye covering device and the magnets pull the eyelid open.

10. The method of claim 4 wherein the eye covering device is an electromagnetic eye covering device and the eyelid is opened and closed by activating the electromagnetic eye covering device.

11. A device comprising:
    an eye covering device;
    an electromagnet incorporated into or affixed to the eye covering device;
    a control circuit in communication with the electromagnet, that is incorporated into or affixed to the eye covering device and configured to tune the electromagnet to generate a field to open or close an eyelid which is associated with a magnet;
    a power supply coupled to the control circuit, that is incorporated into or affixed to the eye covering device, and configured to supply power to the electromagnet under control of the control circuit; and
    a user interface associated with the control circuit, that is incorporated into or affixed to the eye covering device, and configured to receive a user generated control command.

12. The device according to claim 11, wherein the control command includes at least amplitude, length of time and a direction of a current flow, and wherein the control circuit modulates a current and a voltage provided to the electromagnet based upon the control command.

13. A kit comprising:
    a set of pieces of non-particulate magnetic material of appropriate size for affixation to an eyelid or orbital rim; and
    an adhesive appropriate for atraumatic temporary affixation of said non-particulate magnetic material to skin.

14. The kit according to claim 13, further comprising:
    instructions for using said non-particulate magnetic material and adhesive for treating an eyelid disorder.

15. A kit comprising:
    a set of pieces of magnetic material of appropriate size for affixation to an eyelid or orbital rim;
    an eye covering device, wherein electromagnetic material is incorporated into or affixed to the eye covering device; and
    adhesive appropriate for atraumatic temporary affixation of said magnetic material to skin.

16. The kit according to claim 15, further comprising:
    instructions for using said magnetic material, eye covering device, and adhesive for treating an eyelid disorder.

17. A kit comprising:
    magnetic powder configured for application to an eyelid or orbital rim; and
    an eye covering device, wherein electromagnetic material is incorporated into or affixed to the eye covering device.

* * * * *